US009839979B2

(12) United States Patent
Todorov et al.

(10) Patent No.: US 9,839,979 B2
(45) Date of Patent: Dec. 12, 2017

(54) SYSTEM FOR EVALUATING WELD QUALITY USING EDDY CURRENTS

(71) Applicant: EDISON WELDING INSTITUTE, INC., Columbus, OH (US)

(72) Inventors: Evgueni I. Todorov, Dublin, OH (US); Jacob Hay, Circleville, OH (US)

(73) Assignee: Edison Welding Institute, Inc., Columbus, OH (US)

( * ) Notice: Subject to any disclaimer, the term of this patent is extended or adjusted under 35 U.S.C. 154(b) by 123 days.

(21) Appl. No.: 14/978,747

(22) Filed: Dec. 22, 2015

(65) Prior Publication Data

US 2016/0178581 A1 Jun. 23, 2016

Related U.S. Application Data

(60) Provisional application No. 62/233,588, filed on Sep. 28, 2015, provisional application No. 62/095,534, filed on Dec. 22, 2014.

(51) Int. Cl.
| | |
|---|---|
| *B23K 31/12* | (2006.01) |
| *B23K 9/173* | (2006.01) |
| *B23K 31/02* | (2006.01) |
| *B23K 26/21* | (2014.01) |
| *B23K 103/10* | (2006.01) |
| *B23K 103/20* | (2006.01) |
| *B23K 103/04* | (2006.01) |
| *G01N 27/90* | (2006.01) |

(52) U.S. Cl.
CPC ............ *B23K 31/125* (2013.01); *B23K 9/173* (2013.01); *B23K 26/21* (2015.10); *B23K 31/02* (2013.01); *B23K 2203/05* (2015.10); *B23K 2203/10* (2013.01); *B23K 2203/20* (2013.01); *G01N 27/90* (2013.01)

(58) Field of Classification Search
USPC .................................... 324/238, 240, 750.12
See application file for complete search history.

(56) References Cited

U.S. PATENT DOCUMENTS

| | | | | |
|---|---|---|---|---|
| 5,902,935 A | * | 5/1999 | Georgeson | ......... G01N 29/2412 73/801 |
| 2005/0017713 A1 | * | 1/2005 | Goldfine | .............. B23K 20/122 324/240 |

* cited by examiner

*Primary Examiner* — Vincent Q Nguyen
(74) *Attorney, Agent, or Firm* — Frost Brown Todd LLC

(57) ABSTRACT

Electromagnetic and eddy current techniques for fast automated real-time and near real-time inspection and monitoring systems for high production rate joining processes. An eddy current system, array and method for the fast examination of welds to detect anomalies such as missed seam (MS) and lack of penetration (LOP) the system, array and methods capable of detecting and sizing surface and slightly subsurface flaws at various orientations in connection with at least the first and second weld pass.

14 Claims, 15 Drawing Sheets

SYSTEM FOR EVALUATING WELD QUALITY USING EDDY CURRENTS

CROSS-REFERENCE TO RELATED APPLICATIONS

This patent application claims the benefit of U.S. Provisional Patent Application Ser. No. 62/095,534 filed on Dec. 22, 2014 and entitled "System for Evaluating Weld Quality Using Eddy Currents", and of U.S. Provisional Patent Application Ser. No. 62/233,588 filed on Sep. 28, 2015 and entitled "System for Evaluating Weld Quality Using Eddy Currents", the disclosures of which are hereby incorporated by reference herein in their entirety and made part of the present U.S. utility patent application for all purposes.

STATEMENT REGARDING FEDERALLY-FUNDED RESEARCH

This invention was made with government support under Subcontract No. 00132415 issued by Battelle Energy Alliance operating under U.S. Government Contract No. DE-AC07-05ID14517 awarded by the United States Department of Energy. The government has certain rights in the invention.

BACKGROUND OF THE INVENTION

Fusion welding is welding process used to join (i.e., fuse) two or more pieces of metal by causing the metal to reach its melting point. The process typically involves the use of a filler metal, provided by a consumable electrode or a wire, and a flux, which protects the molten metal of the weld from the damaging effects of the atmosphere. Fusion welding is utilized in numerous industries, including the oil and gas sectors, the energy industry, light and heavy manufacturing operations and the aerospace industry. There are several types of fusion welding processes, including arc welding, electric resistance welding, oxy-fuel welding and thermite welding, as well as certain advanced and high production rate joining processes, including laser-beam welding combined with gas-metal-arc welding (LBW/GMAW), also known as hybrid laser gas metal arc welding (HLGMAW). Due to the high-temperature phase transitions inherent in these processes, a heat-affected zone is created in the welded material. Because fusion welds often encounter significant loads and fatigue during the lifetime of a welded product, there is a chance that such welds may fail if not created to proper specifications. For example, the base metal must reach a certain predetermined temperature during the welding process, must cool at a specific rate, and must be welded with compatible materials or the joint may not be strong enough to hold separate parts together or cracks may form, thereby causing the weld to fail. Common welding defects such as lack of fusion (LOF) of the weld to the parent metal, cracks or porosity inside the weld, and variations in weld density may cause a structure to fracture and break or a pipeline to rupture. Accordingly, inspecting such welds after their creation is an important aspect of preventing the failure of welded products.

Fusion welds may be tested using non-destructive evaluation techniques such as visual inspection; industrial radiography or industrial computer tomography (CT) scanning using X-rays or gamma rays; ultrasonic testing; liquid penetrant testing; magnetic particle inspection; or by eddy current. In a proper weld, these tests would indicate a lack of volumetric (pores, undercut, under-fill etc.) defects in a resultant radiograph, show clear passage of sound through the weld and back, or indicate a clear surface without penetrant captured in cracks. However, the detection of transverse discontinuities is very difficult with existing ultrasonic equipment, and the various techniques currently applied require that welding equipment be removed to conduct post-weld non-destructive evaluation. Removing the welding equipment often causes delay in the welding process and creates additional fabrication and examination delays if unacceptable discontinuities are detected which require repair or re-examination. Thus, there is an ongoing need for a more efficient, less disruptive system and method for conducting non-destructive evaluation of fusion welds for quality assurance. More particularly, there is a need in the art for an approach for real- or near-real time weld monitoring of joining process such as HLGMAW whereby analyses can be done during fabrication.

SUMMARY OF THE INVENTION

The following provides a summary of certain exemplary embodiments of the present invention. This summary is not an extensive overview and is not intended to identify key or critical aspects or elements of the present invention or to delineate its scope.

Provided are eddy current (EC) systems and methods for non-destructively inspecting joints post, real-time or near-real time during joining processes. A key disadvantage of conventional EC techniques is the high degree of sensor specialization and high skill level required for operators. The introduction of well-designed automated systems, as disclosed herein, compensate for this disadvantage. Further, the physical limitation of alternating EC excitation results in reduction of the electromagnetic field strength away from the test object surface resulting in rapidly decreasing sensitivity and resolution to subsurface flaws at increasing depth. The disclosed methods herein overcome that deficiency by enabling use of EC techniques in multiple welding passes through adaptations to the sensor receiver and exciter designs, and the integration of the sensor in line for near or real time monitoring of welding.

The present invention permits real-time weld monitoring to detect critical surface and subsurface flaws during actual welding. Unlike conventional approaches to weld analysis, according to the instant disclosure, each weld pass can be analyzed in process providing additional examinations and evaluations not currently available in the art, enabling adjustments to the welding process when the welded parts are still in the weld fixture. Costly repairs can be avoided, and risk of weld failure significantly reduced. Accordingly, the systems and methods disclosed herein significantly reduce or eliminate the need for post weld examination, and can improve process productivity by at least two to four times.

Key advantages of this invention include: (i) real-time inspection of welds with little or no preparation of the test surface; (ii) elimination of couplants or environmentally unfriendly cleaners and etchants; (iii) high speed, non-contact, complete inspection of each weld pass length and volume; (iv) elimination or reduction of destructive testing and sampling; (v) elimination or significant reduction of post-weld non-destructive evaluation; (vi) the ability to work on hot surfaces; (vii) providing real-time feedback to the welding system for correcting the welding process, when necessary; (viii) detection of longitudinal and transverse discontinuities with a single pass; (ix) examination of the weld, heat affected zone, and the parent metal simultaneously with a single pass; and (x) the use of air for cooling purposes.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein.

DETAILED DESCRIPTION OF THE INVENTION

Figure 1A:
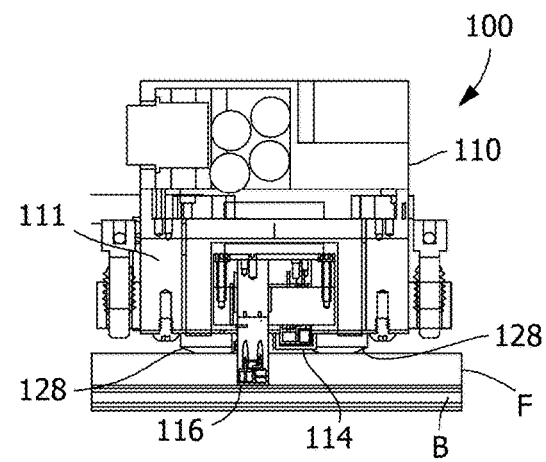
FIG. 1A is a graphic illustration of a side cross-sectional view of an exemplary eddy current sensor array during scanning of the first pass.

Fusion welding processes typically require several welding passes for effectively depositing the required metal. For example, flaw types that may be expected during HLGMAW include, but are not limited to, solidification cracks at center line (CL); lack of penetration (LOP) due to low power and/or high speed; excessive metal drop through root due to high power and/or low speed; LOF; inter-bead lack of fusion (IBLOF); and pores. In some instances, weld flaws might be open to the top and bottom surfaces or located mid-wall like solidification cracks. Planar flaws like LOF and LOP would be more critical for service fitness than pores.

Detecting these various discontinuities is very difficult with existing ultrasonic equipment and the welding apparatus must usually be removed to conduct post-welding non-destructive evaluation, either between passes, or after welding is complete. Several non-destructive evaluation techniques, including one or more of visual, ultrasonics, liquid penetrant, magnetic particles, eddy current, radiography are often required to examine the entire weld volume after welding is complete. This aspect of quality assurance may cause delays in the overall manufacturing process and can create additional fabrication and examination delays if unacceptable discontinuities are detected and repair and re-examination is then required.

To address the shortcomings in the art, an eddy current (EC) system was developed to employ one or multiple sensors for monitoring of various material and geometry conditions for detection of flaws during one or more of a variety of welding process, such as, laser-beam welding, gas-metal-arc welding, and a hybrid laser gas metal arc welding (HLGMAW). One advantage of EC techniques is that they do not require direct contact with the test object or couplant to transmit the energy. Thus, in accordance with the various embodiments of the invention, inspection of fast moving and hot surfaces such as hot-rolled wires, slabs, plates, welds, and others can be achieved.

By varying the excitation frequency and probe configurations, the electromagnetic sensors can detect surface and subsurface flaws, some even relatively small. Advantageously, in addition to flaw length, signals are correlated to flaw depth a. Further, the EC techniques are also sensitive to changes in metallurgical phase composition, hardness, residual stresses, and any other conditions that will affect the electrical conductivity and or magnetic permeability. The EC sensors produce electrical signals that are easily acquired, transmitted, and processed. Therefore, the electromagnetic techniques are fast (several inches per second inspection speed are not unusual), reliable, and perfectly suited for building real-time monitoring automated systems.

The system and method of the present invention significantly reduces post welding non-destructive evaluation requirements by examining the entire volume of each successive weld pass for critical surface and subsurface discontinuities and/or problematic conditions in any orientation. This invention also permits fast repair and reexamination of the repair while the welded part is still mounted in the welding fixture. According to various embodiments, the sensor is positioned in-line, and close behind to follow the laser head for real- or near-real time monitoring. The sensor as disclosed herein is capable of detecting surface and subsurface flaws in the first, second, and any subsequent pass. This is in contrast to conventionally applied EC monitoring of cold welds, wherein only the top or cap surface of each pass would be accessible for testing, and wherein access to the top surface of a first pass would further be particularly impeded by the narrow bead preparation.

Exemplary embodiments of the present invention are now described with reference to the drawings. Although the following detailed description contains many specifics for purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed inventions.

Figure 1B:
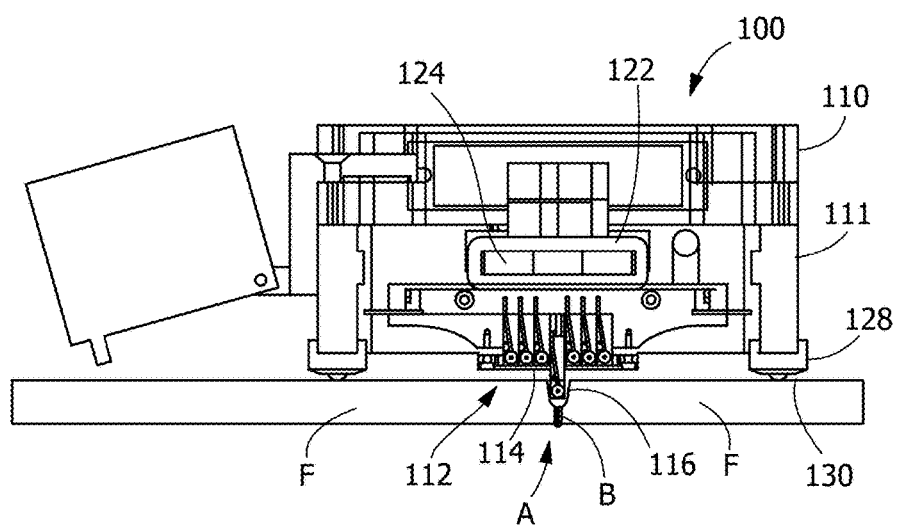
FIG. 1B is a graphic illustration of a front cross-sectional view of an exemplary eddy current sensor array during scanning of the first pass.
Figure 1C:
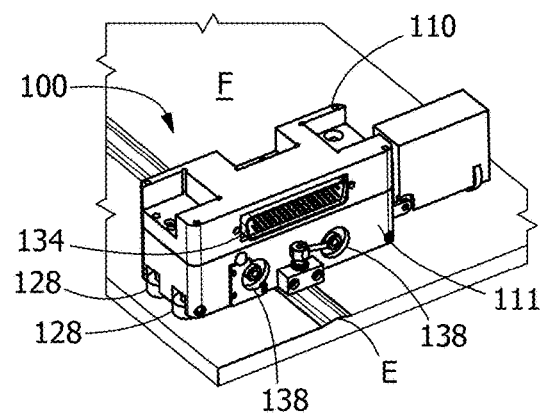
FIG. 1C is a graphic illustration of a rear perspective view of an exemplary eddy current sensor array during scanning of the first pass.

Referring now to the drawings, FIGS. 1A-C show in three alternate views, from left to right, a side cross sectional view, a front cross-sectional view, and a rear perspective view of an exemplary eddy current sensor array 112 during scanning of the first weld pass B. As further described herein, eddy current sensor 100 includes upper housing 110 and lower housing 111 and other related components and elements. Good results were obtained using an aluminum alloy for the housing components, though one of ordinary skill would appreciate that alternate materials could be selected having sufficient heat resistance, good electrical conductivity, and other desirable properties suitable for use in a welding shop. Examples of alternate materials include magnetic carbon steel and non-magnetic alloys such as copper and brass.

In accordance with the disclosure, as further described herein below, the present invention includes systems and methods for weld analysis including a first mode of operation, wherein, in a particular embodiment, a single sensor element 114 consisting of two orthogonal X and Z receiver coils, 118 and 120, is used for inspecting first pass B or passes in narrow beads/grooves. Sensor element 114 is adapted for positioning in close proximity to weld joint A to provide critical information within the depth of the joint relative to the initial weld pass B. According to some embodiments, sensor element 114 does not touch the surface being evaluated. While in use it is most advantageous to employ the first mode of operation in line with the joining equipment on a hot weld, it is possible to inspect both hot and cold welds.

In a second mode of operation, a sensor array 112 of two or more receiver (sensor) elements 114 consisting of two orthogonal X and Z receiver coils, 118 and 120, is used for inspection of second pass C or wide open beads D. The receiver elements 114 do not touch the surface being evaluated and the array contour is initially shaped or fixed to follow weld contour of hot or cold welds. It is possible to inspect both hot and cold welds with this embodiment. As further described herein below, variations on these modes of operation are possible, particularly for use in line with joining equipment, whereby more receiver elements 114 may be employed in the first mode of operation, and more or fewer receiver elements 114 may be employed in the second mode of operation. Further, while it is contemplated that the first mode is employed for a first joining pass, and the second mode for second and subsequent joining passes, it will be appreciated that the systems and methods may be employed for only a first pass either in line with the weld system or offline, and likewise may be used only for second and subsequent passes, in process or post process, or combination of these.

General features and advantages include: (i) single element 116 and array 112 need not touch the hot weld surface; (ii) single element 116 and array 112 detect both surface and subsurface discontinuities in each pass; (iii) retractable bead guides 132 are provided for first pass or narrow groove welds to guide sensor element 116 in the groove (weld area A) and prevent damage to the element in the groove; and (iv) adjustable spacers 128 with rollers are provided for adjusting sensor element clearance to weld hot or cold surface.

Figure 2:
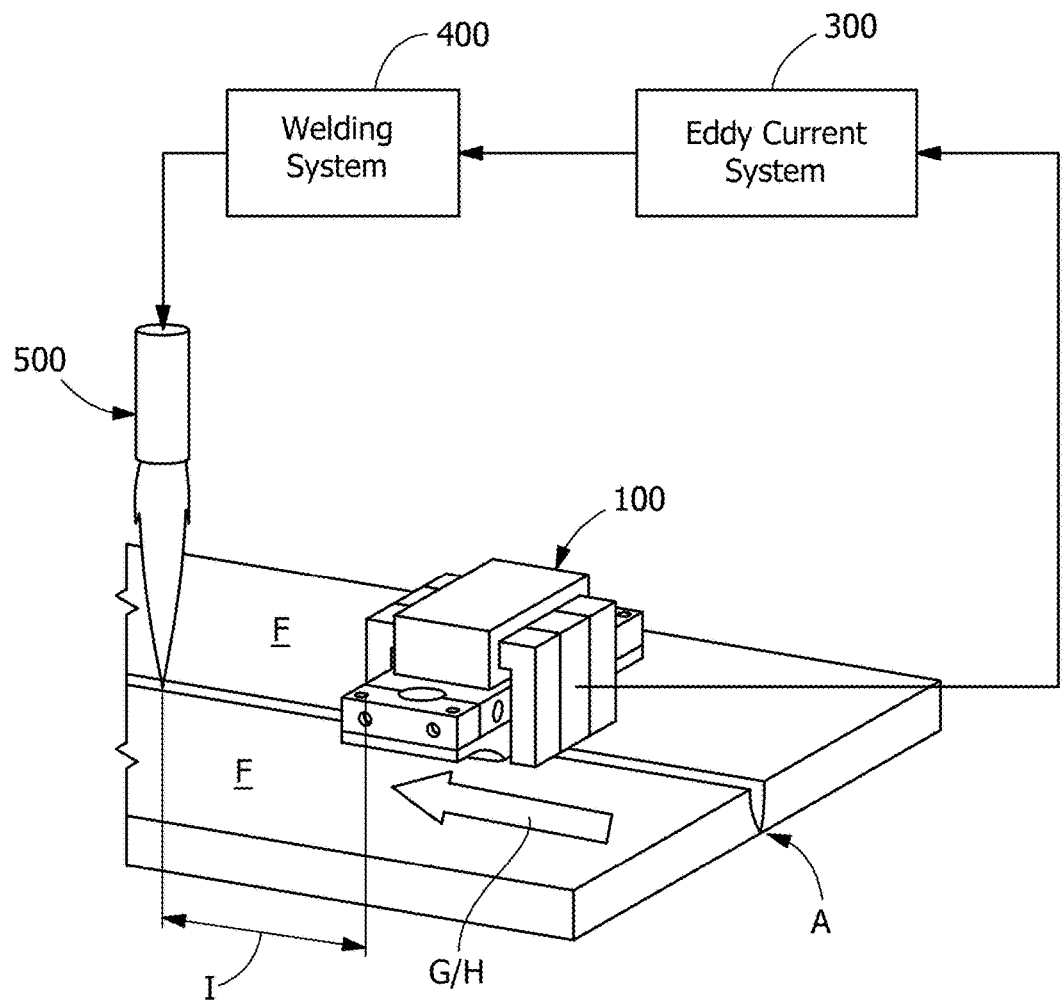
FIG. 2 is a graphic illustration of a weld system with an exemplary eddy current weld evaluation system arranged in line utilized for real-time monitoring of a welding process.

With reference to FIG. 2, eddy current sensor 100 is capable of closely following the weld pass and weld bead surface, wherein sensor array 112 is positioned in close proximity to and behind weld torch 500. According to some embodiments, sensor elements 114 do not touch the weld surface during the scanning of the first and second passes (B and C), allowing weld examination closely following weld torch 500 without detrimental effect to the receiver elements 114 due to the high heat. In some embodiments, air-cooling is provided through at least one cooling element (line) 140. Sensor array 112 follows the bead contour regardless of whether the bead is narrow or wide (e.g., V-shape). The array also follows the weld crown surface when completed and is raised above the parent metal surface. According to some embodiments, at least one receiver element 116 of sensor array 112 is extended in a downward (vertical) direction for improved proximity to the weld joint for first pass B, receiver element 116 positioned in as close proximity as possible without contacting the metal surface to avoid heat damage. It will be appreciated that the specific height may vary depending on the variability of the weld cap and the heat tolerance of the receiver element materials. Likewise, for scans after the first pass, in some embodiments, the at least one receiver element 116 is retracted and is positioned in proximity to the surface to minimize heat damage. According to the various embodiments, examination is conducted after each weld pass by closely following weld torch 500, thereby allowing for reliable scanning of the entire weld pass volume for surface and subsurface discontinuities.

Figure 3A:
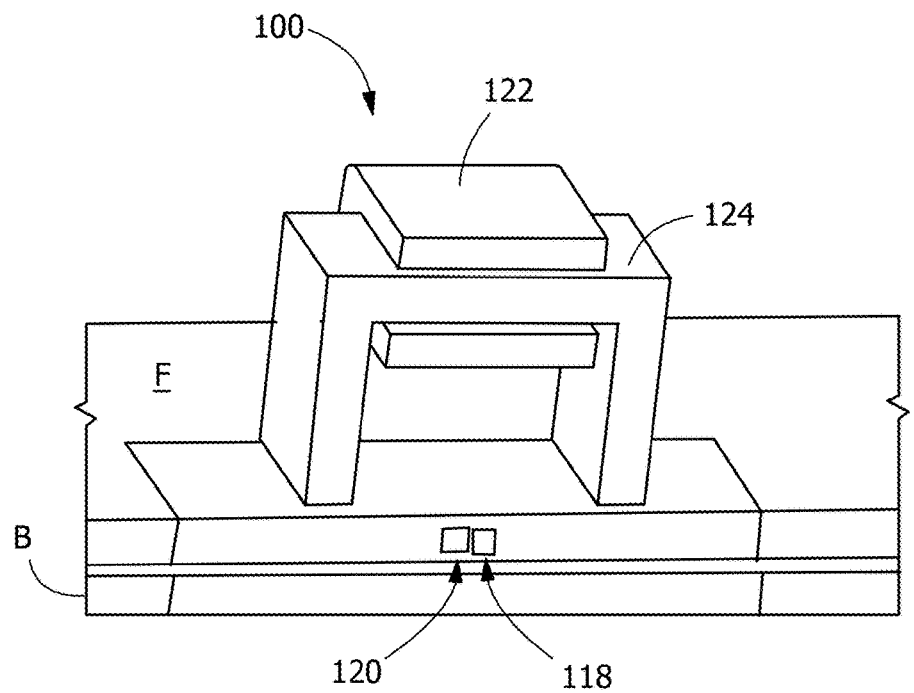
FIG. 3A is a graphic illustration of an eddy current weld evaluation system in accordance with an exemplary embodiment of this invention, wherein eddy current density is shown in (a) the weld with the first pass.
Figure 3B:
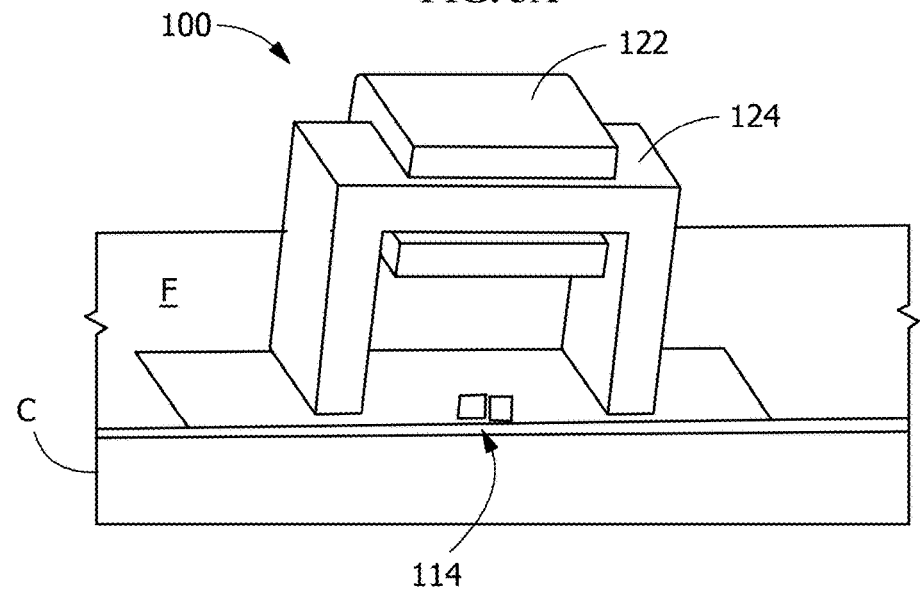
FIG. 3B is a graphic illustration of an eddy current weld evaluation system in accordance with an exemplary embodiment of this invention, wherein eddy current density is shown in the weld with the second pass.
Figure 4:
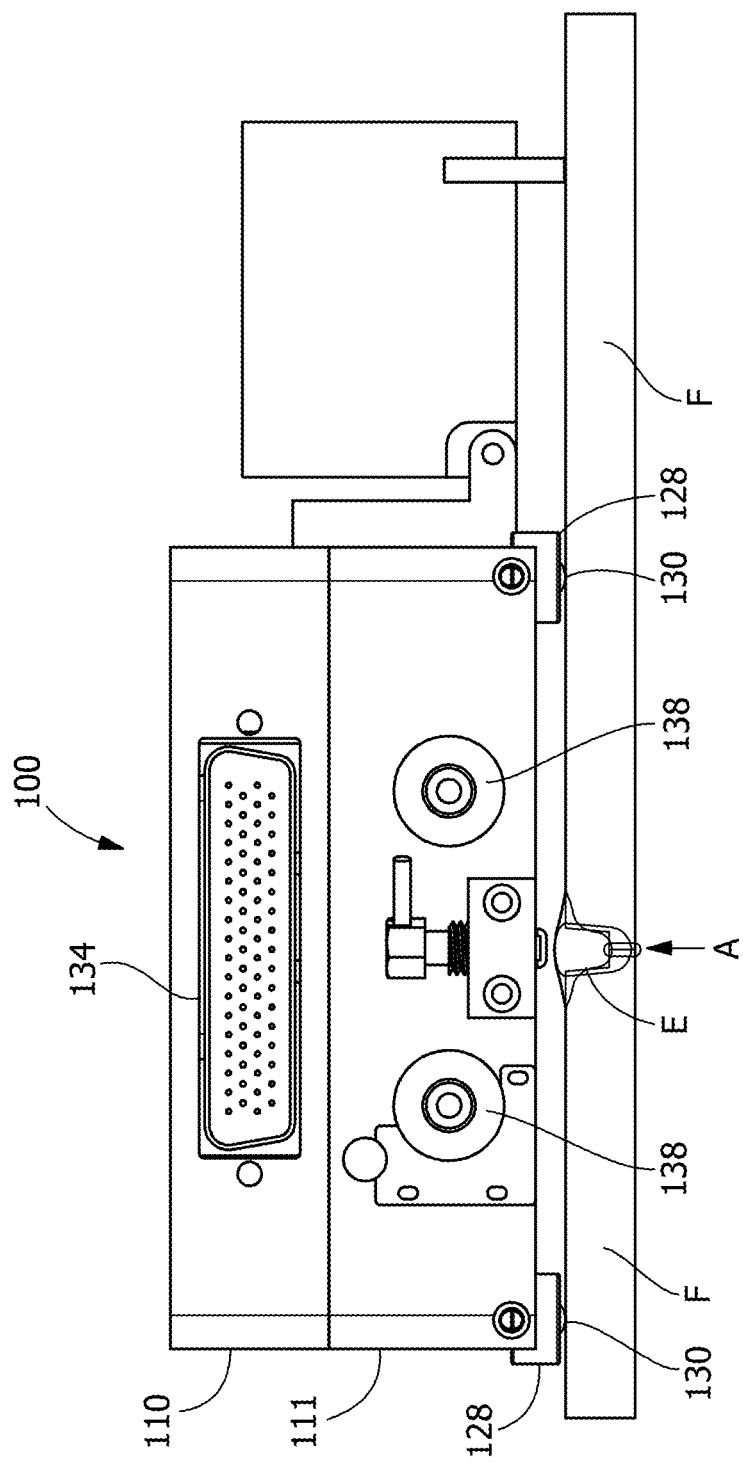
FIG. 4 is a graphic illustration of an alternate front view of an eddy current weld evaluation system arranged in line with a weld and a receiver array is extended.
Figure 5:
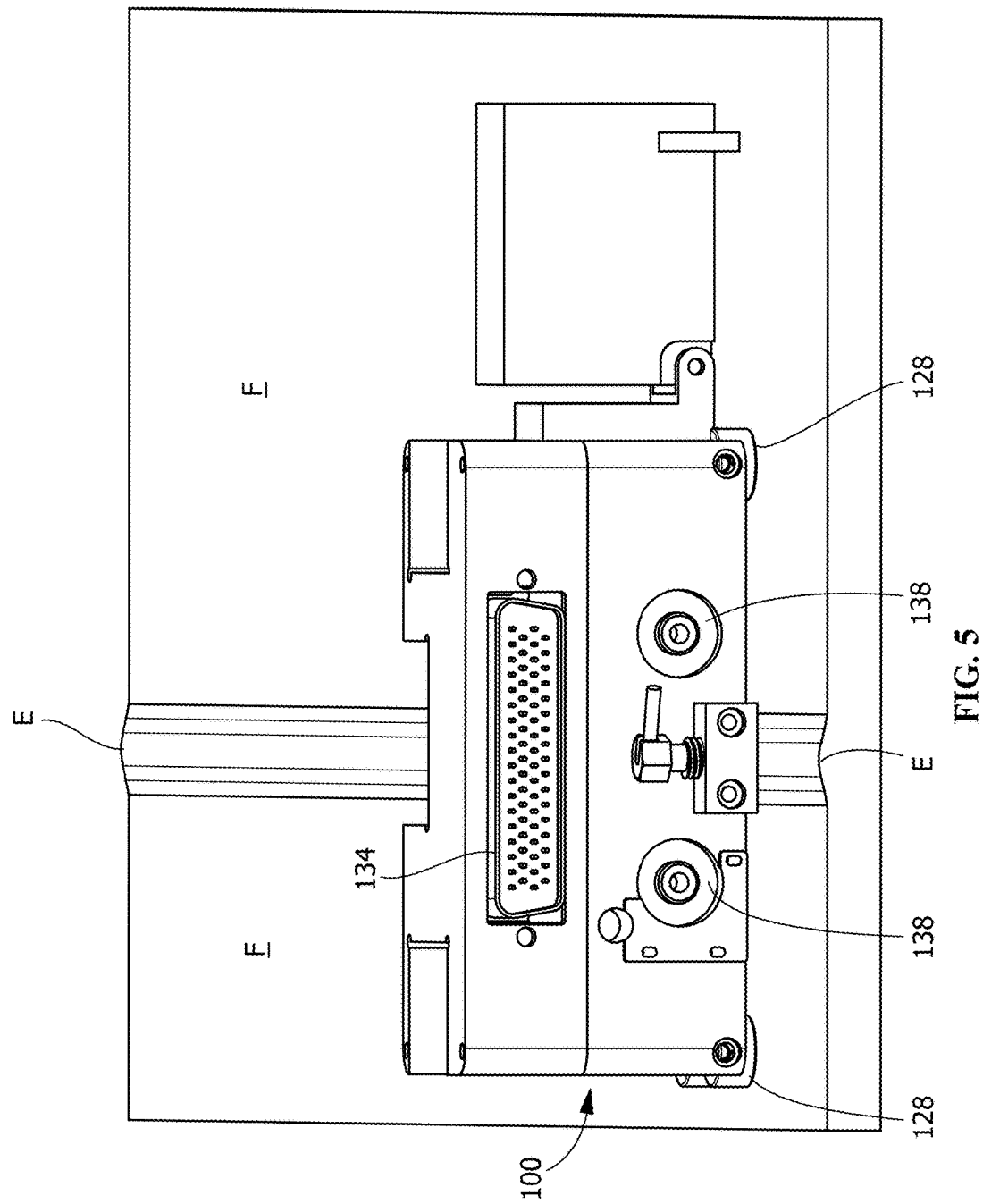
FIG. 5 is a graphic illustration of an alternate front elevated view of an eddy current weld evaluation system arranged in line with a weld.
Figure 6:
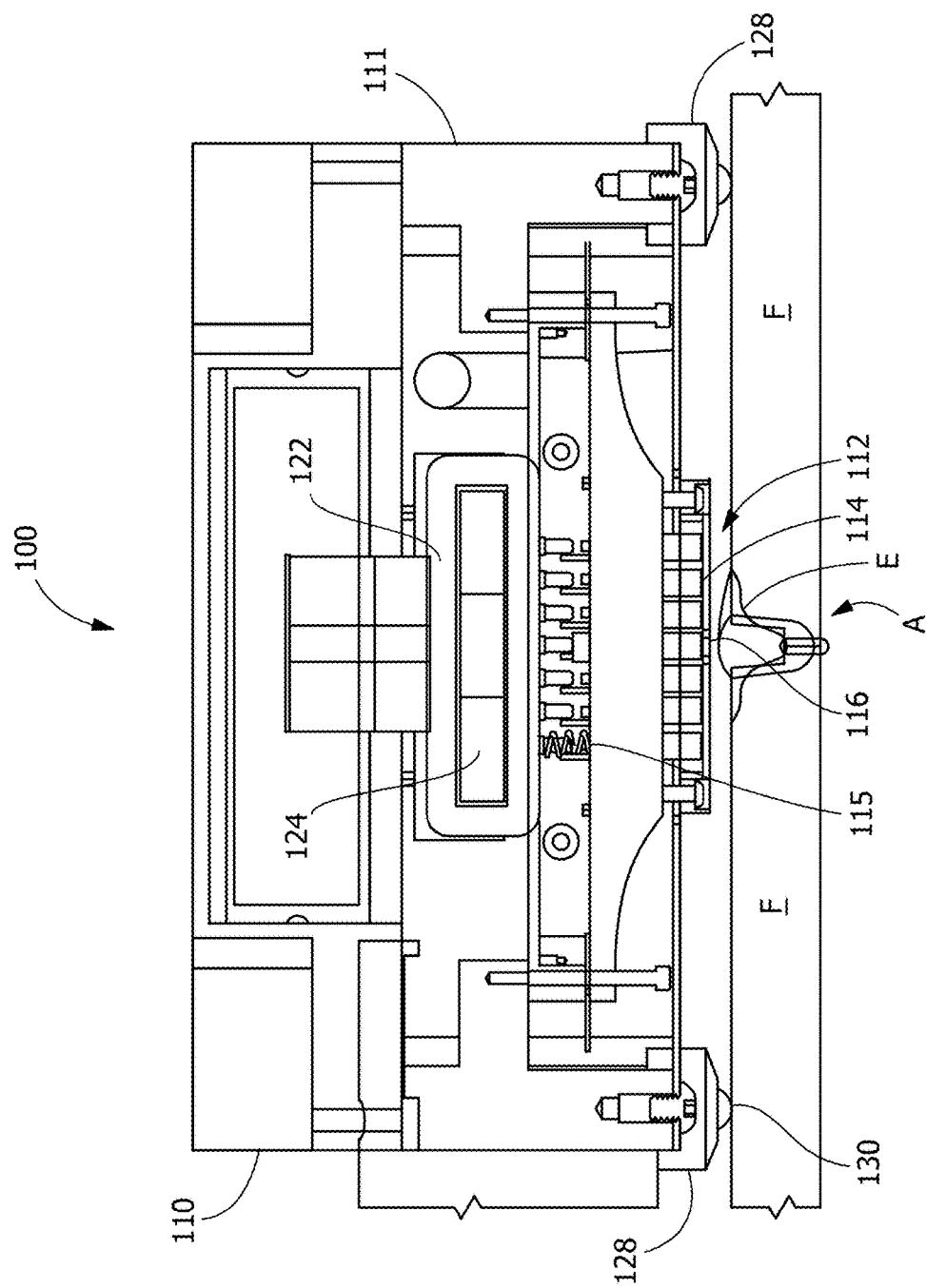
FIG. 6 is a graphic illustration of an alternate front cross sectional view of an eddy current weld evaluation system arranged in line with a weld and a receiver array is extended.
Figure 7:
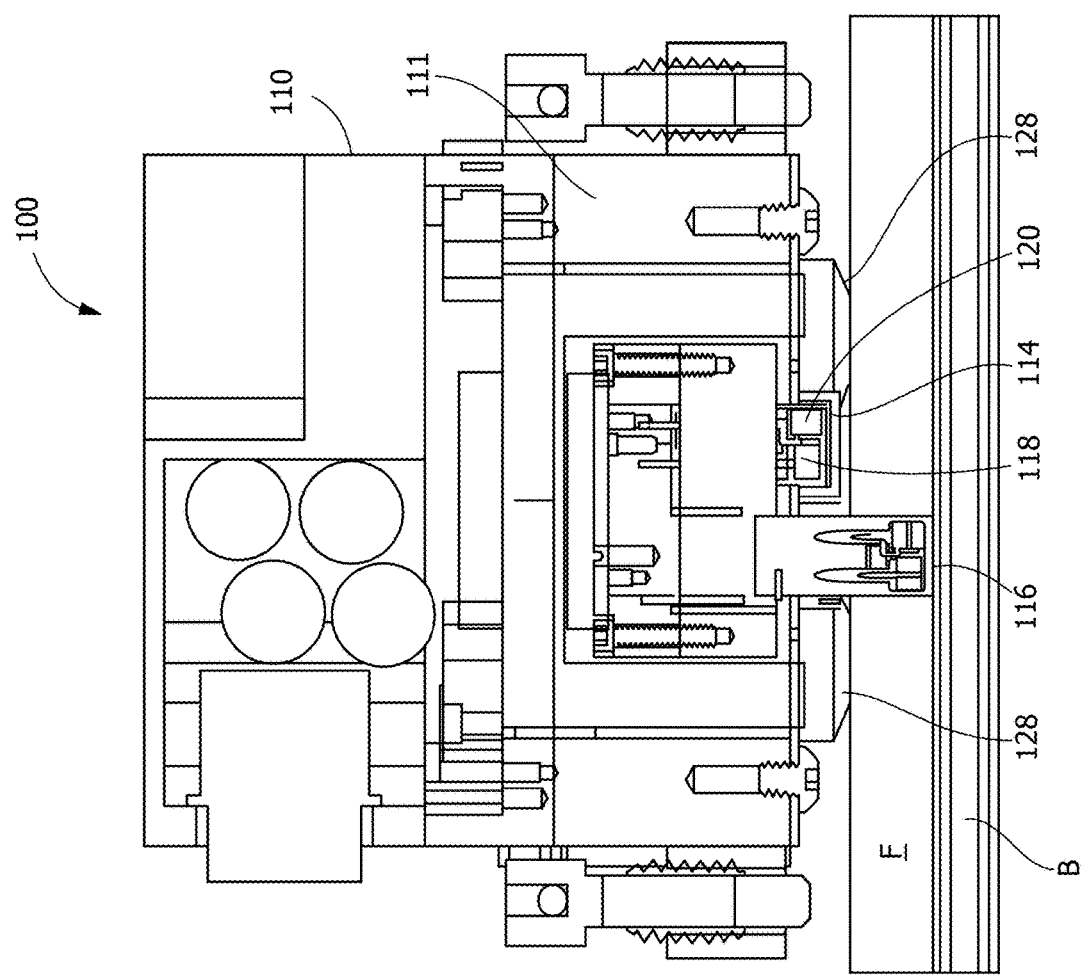
FIG. 7 is a graphic illustration of an alternate side cross sectional view of an eddy current weld evaluation system arranged in line with a weld and cross sectional view of a receiver element.
Figure 8:
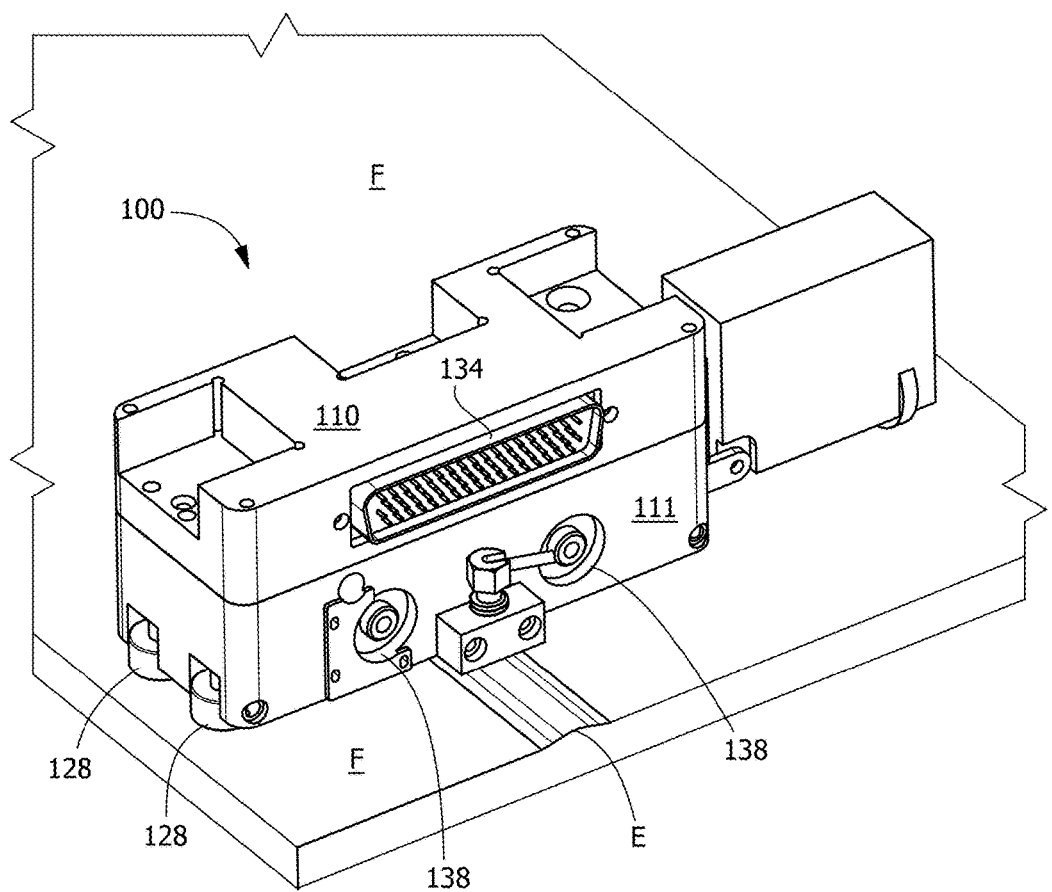
FIG. 8 is a graphic illustration of an alternate a rear perspective view of an eddy current weld evaluation system arranged in line with a weld.

Referring again to the drawings, FIG. 3 depicts an exemplary embodiment of sensor elements 114 of eddy current sensor 100 according to the disclosure, wherein changes in eddy current density are evaluated in a first weld pass B and in the weld in a second weld pass C. As depicted, the exemplary embodiment includes a single large substantially U-shaped exciter element 122 comprising ferrite core 124 wrapped with a copper coil, as more fully described herein below. Eddy current sensor 100 also includes individual sensor elements 114 comprising two orthogonally oriented receivers 118 and 120 formed of copper coil. As more fully described herein below, other exemplary embodiments of eddy current sensor 100 are contemplated herein, wherein the receiver component comprises an array 112 of at least two receiver (sensor) elements 114. Referring again to FIG. 3 according to the depicted embodiment, an eddy current sensor 100 in transmit-receive arrangement having a single large exciter coil 122, as shown, has been shown to provide good them al stability and high depth of penetration (DP). Exciter coils that induce eddy currents with sufficient density and contour shape necessary for reliable flaw detection in the inspected part comprise a large single exciter coil 122, and comprise a ferrite core 124 within coil 122. In some embodiments, the exciter shape includes a coil with "U"-shape ferrite concentrator core, and in other embodiments the exciter shape includes a coil with rectangular or "I"-shape ferrite field concentrator. In accordance with some embodiments, the shape of the concentrator core can affect field concentration, flux, and edge effect. In some embodiments, good results are obtained with a U-shape concentrator for providing good field concentration with minimum flux losses and smaller edge effect as compared with an I-shaped concentrator.

Referring again to FIG. 3, as depicted, eddy current sensor 100 is shown in a side cutaway view parallel to weld joint A, and depicting the relative positions of exciter 122 and receiver elements 114, in which an exciter coil is wound on a U-shape ferrite to generate an alternating electromagnetic field through the entire volume of the weld and parent metal F surrounding weld. The alternating magnetic field generates eddy currents in parent material F and in weld itself. The eddy current density and distribution depends on the electromagnetic properties of parent material F and weld (e.g., magnetic permeability and electrical conductivity), field frequency, and geometry of the field concentrator and coil.

Changes in the eddy current electromagnetic field caused by changes in weld properties and the presence of discontinuities are registered with two types of receivers 118 and 120, according to the embodiment as shown in FIG. 3. According to various embodiments, one or more receivers in an element 114 or array 112 may be formed of one or more coils wound with a good electrical-conductor wire, a coil having a ferrite core, a giant magnetic resistive sensor, and a Hall effect sensor.

As depicted in the exemplary embodiment shown in FIG. 3, receivers 118 and 120 comprise coils, first type of receiver sensors (Z-coils) 120 register field changes normal to a weld pass while a second type of receiver sensors (X-coils) 118 register field changes parallel to the weld pass. While both coils are sensitive to discontinuities parallel to the weld length, the X-coils are also sensitive to the magnetic flux leakage caused by transverse weld discontinuities. Receiver coils are grouped into elements such that each element contains one Z- and one X-receiver, as shown in FIG. 3.

FIGS. 4-8 show alternate views of the housed sensor elements of the representative embodiments of the eddy current sensor array 112 shown in FIG. 1-FIG. 3.

Exciter coils with large number of turns and ferrite cores were found to be particularly useful for providing flaw signals with sufficient strength at low frequencies. Further, as show in the exemplary embodiment in FIG. 3, relatively small receivers formed of coils and arranged in orthogonally positioned pairs which can range in size from between $\frac{1}{100}$ to $\frac{1}{10}$ the size of the exciter element provide a high degree of sensitivity and are capable of being positioned in close approximation to the surface of the weld material. The relative sizes of the receiver and exciter elements, the shape and size of the exciter, and the orthogonally oriented receivers enable sufficient signal strength and sensitivity to identify relatively deep defects in a weld bead or cap. This type of configuration also allows detection of defects without contacting the surface of the weld material, thus enabling near or real time monitoring of weld creation and the ability to adjust in real time. According to various embodiments, the receiver elements may be positioned from as close as micrometers from the weld surface up to as much as 10 mm away from the weld surface. Thus, the distance of the receiver elements may be from at the surface, to 0.1 mm to 1, 2, 3, 4, 5, 6, 7, 8, 9, 10 mm and increments in between. It will be appreciated that the various parameters of element proportions, material selection, and distance from weld surface, as well as overall element size may be varied depending on the geometry of the weld material.

Thus, according to the various embodiments, the specific dimensions and configuration of sensor electrical components (e.g., coils, ferrite concentrator) may be varied and adapted to accommodate specific weld conditions. As an aspect of development of the inventive systems and methods herein, the sensor component parameters were optimized and determined virtually with finite element software, and subsequently implanted for demonstration. The configurations were predicted by modeling to enable adequate depth of penetration to be achieved to test each weld pass. According to the modelling, planar and volumetric flaws with heights of 1.5 mm and larger would be detectable. It will thus be appreciated that similar modeling could be employed to provide alternate specifications.

Figure 11:
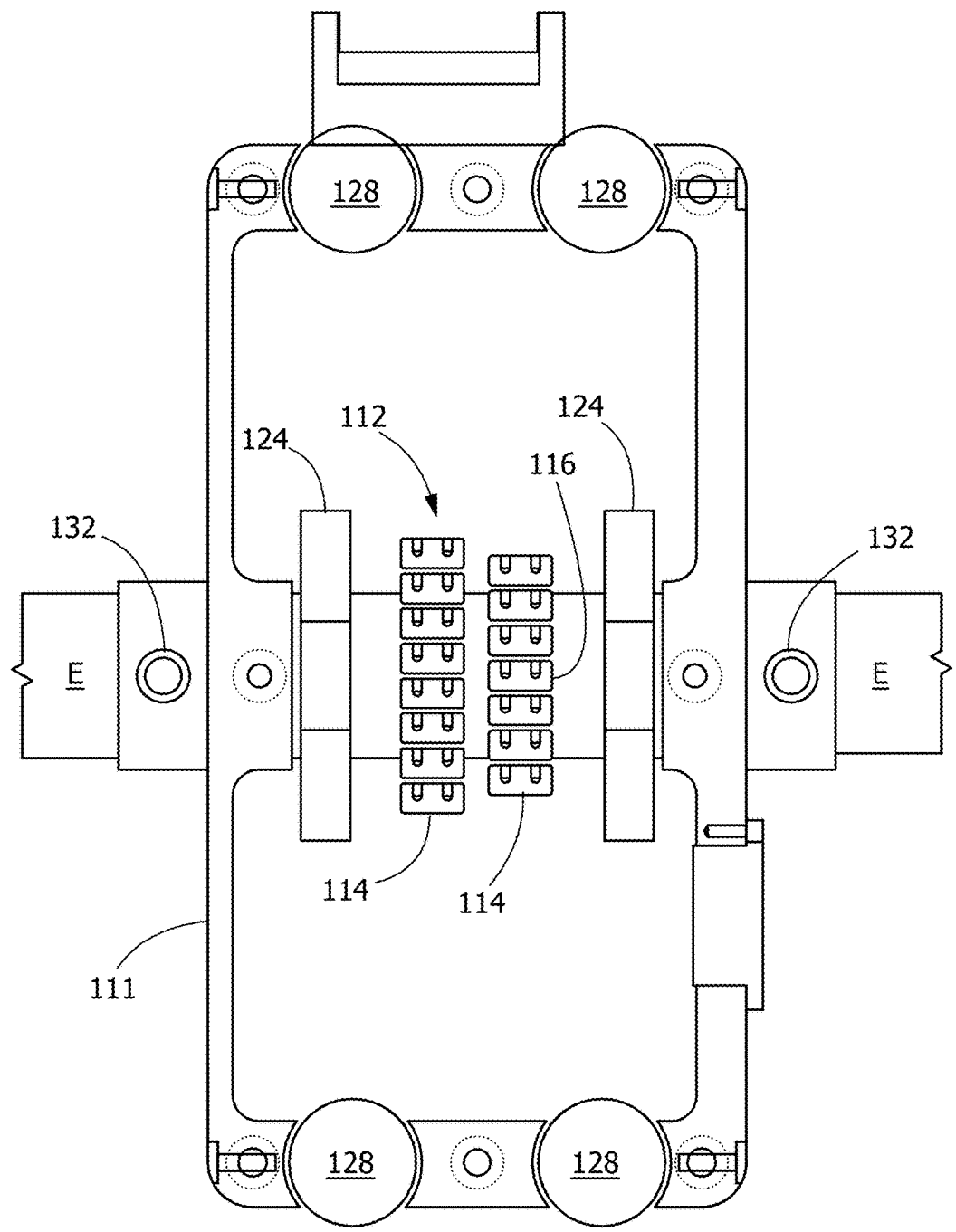
FIG. 11 provides a graphic scheme for an array of receiver elements depicted oriented in line with a weld.

In various embodiments, the number of sensor exciter and receiver components may be varied. While the disclosure shows examples of working embodiments having a single exciter and an array of multiple receiver elements, other embodiments are contemplated and possible. Accordingly, more than one and up to several exciter elements may be used, wherein in some alternate embodiments that include multiple exciter elements, the arrangement of these may be from one (1) to 20 elements, and in some embodiments from 7 to 15 elements where one predetermined receiver coil is linked to an exciter coil. Further, while the depicted embodiments of receiver arrays show fifteen elements, for example as shown in the schematic of FIG. 11, more or fewer may be employed based upon such factors as the degree of sensitivity, the size of the weld joint, and the selection of configuration of the exciter element(s), among others.

Unexpectedly, it was found as an aspect of the inventive method and system that a single receiver can reliably provide data about weld flaws. It was further unexpectedly found that the position of such at least one receiver need not be directly oriented over the weld joint in order to detect a flaw. Indeed, the development trials showed that planar flaws that are parallel to the weld (e.g., LOP and LOF) are detected not only by the sensor element positioned exactly above the flaw, but other sensor elements positioned up to 10 mm (at ~12 dB signal drop) laterally from the flaw position. This finding further validated the predictions of the field models. Thus, while in various embodiments arrays of multiple sensor receivers may be included in the EC system, the system can operate with a minimum number of sensors.

In developing working devices according to the disclosure, this finding allowed reduction from the fifteen Z-channel receiver elements that were initially planned to eight Z-channel receiver elements without adversely affecting detection capabilities. The modeling also indicated that the field spread would increase as the lift off (LO) was increased, though the sensitivity may be reduced. Accordingly, depending on the determination regarding tolerance to sensitivity losses, simple yet efficient arrays could be built with fewer elements or more elements. In particular, use of an exciter coil and field concentrator according to the embodiment having a U-shaped ferrite core, as described herein, would permit use of arrays with the fewest receivers.

In accordance with some embodiments, one or more sensor receiver elements 114 are adapted for actuation by a mechanism that enables deployment in a vertical direction to move the one or more elements 114 into or away from close proximity to a weld joint. Accordingly, in some embodiments, the mechanism comprises actuatable spring 115 whereby one or more receiver elements 114 are spring-loaded and can be positionally adjusted to conform to the weld contour without physical contact. While in some embodiments, the heat tolerance of a selected receiver element 114 may enable physical contact with a hot weld joint for certain periods of time, the mechanism enables retraction to manage heat exposure and to conform generally to the contour of a weld joint. Elements 114 will then retract following the obstacle contour and will return to the initial position after the obstacle is scanned.

In some embodiments, eddy current sensor 100 is adapted with one or more elevation elements that operate to adjust the vertical position of an array of two or more receiver elements 114, and in some embodiments, the entire housing (110, 111) of eddy current sensor 100.

In some embodiments, eddy current sensor 100 comprises one or more cooling elements. According to some such embodiments, air is supplied using air cooling lines 140 to cool one or more of exciter coils 122, receiver elements 114, housing (110, 111), and the weld surface below eddy current sensor 100. According to some embodiments, the air used for cooling eddy current sensor 100 is also blown down through row of holes 126, as shown, for example, in FIG. 9, to the weld surface in front of advancing eddy current sensor 100 providing further reduction of heat transfer from the weld surface to eddy current sensor 100. In some optional embodiments, cooling elements may operate to provide cooling, and to provide mechanical force to the EC sensor components. As disclosed herein, in some embodiments the vertical position of the one or more receiver elements 114 may be controlled with springs 115 or other mechanical means. According to some alternate embodiments, receiver elements 114 are kept in close proximity with the inspected surface by applying appropriate air pressure through air connector 138, and in some such embodiments, the supplied air also serves as a coolant for sensor elements 114 and entire sensor apparatus. According to such specific embodiments, each of one or more spring-loaded sensor elements is capable of moving over cap bumps and touching the hot solidified metal for a short time. Air is supplied for cooling the hot eddy current sensor 100 and the hot metal in front of the advancing eddy current sensor 100.

Figure 12:
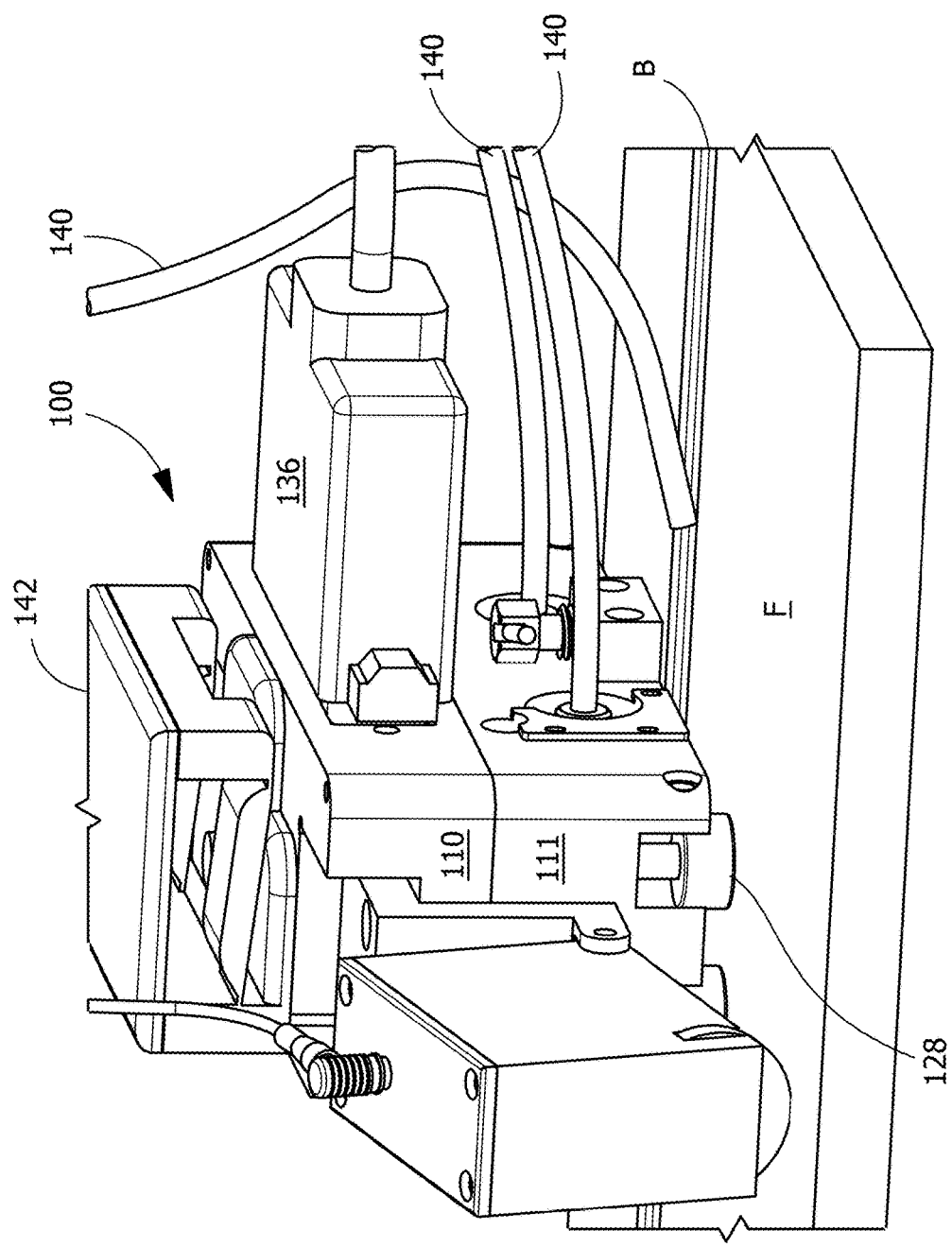
FIG. 12 is a graphic illustration of a weld system with an eddy current weld evaluation system arranged in line.

Using the system and method of this invention, eddy current sensor 100 is configured and integrated with the welding equipment, such as for example a conventional HLGMAW system, whereby the sensor is mounted inline with the HLGMAW components at a position that is behind welding torch 500, as shown, for example in the scheme shown in FIG. 2 and as shown in FIG. 12. While eddy current sensor 100 would be operational for monitoring the weld at the same position as the torch and/or laser, due to the extreme heat its position is selected at a distance that will minimize the exposure of receiver elements 114 to direct heat. Accordingly, good results have been obtained when the elements are exposed to temperatures of 200 degrees C. or below. It will be appreciated that various means may be employed for managing the effects of heat, including selection of material and use of cooling systems. In accordance with some embodiments, sensor components are manufactured from high temperature resistant materials so that the eddy current sensor 100 may be placed as close as possible to welding torch 500. In some particular embodiments, the materials are suitable for exposure to temperatures up to 200° C. Of course, it will be appreciated by one of ordinary skill that the type and availability of materials for the receiver elements will influence the ultimate thermal resistance possible for receiver/sensor elements 114, according to the disclosure.

As has been described with respect to some exemplary embodiments herein, eddy current sensor 100 can be implemented to provide multiple modes of operation. Two modes of operation were demonstrated—scanning of first pass and array scan of larger area. In trials as described herein, eddy current sensor 100 was connected to off-the-shelf multiplexer working with MS5800 eddy current instrument and MultiView software for data processing and imaging. It will be appreciated that the selection of instruments and software for control and analysis are within the skill in the art.

Figure 9:
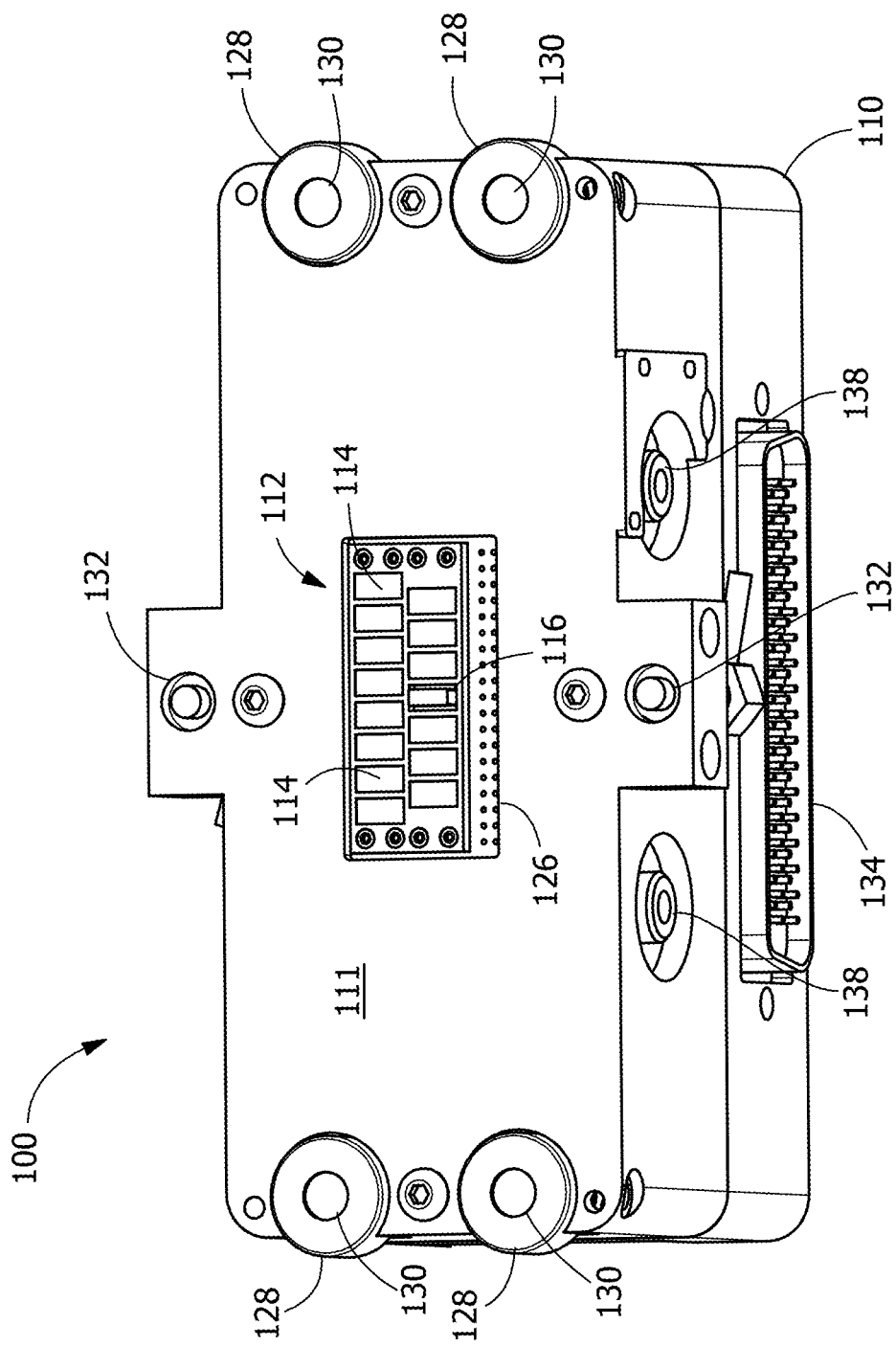
FIG. 9 is a bottom perspective view of an eddy current weld evaluation system, showing extended front and rear face guides, and a single extended sensor receiver element for the first pass.
Figure 10:
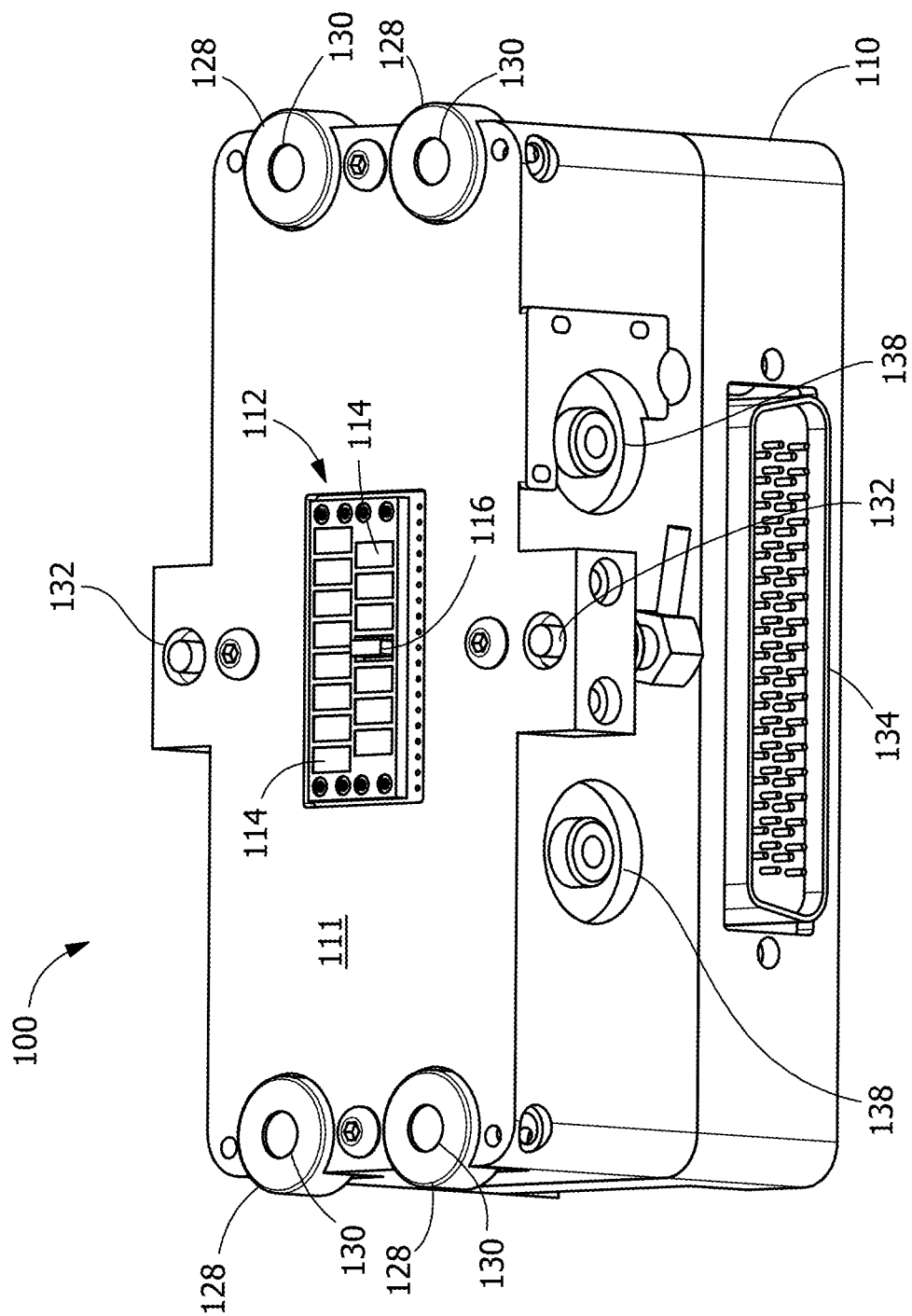
FIG. 10 is a graphic illustration of an alternate bottom perspective view of an eddy current weld evaluation system, showing retracted front and rear face guides and sensor receiver element and extended elevation system spacers and rollers.

Referring again to the drawings, FIG. 9 and FIG. 10 each show alternate operating arrangements for an exemplary eddy current sensor array 112, wherein sensor elements 114 are spring-loaded which allows implementation of multipurpose scanning patterns, including but not limited to the use of single sensor element 116 for scanning the first pass and one or more sensor elements 114 selected from sensor array 112 for secondary and later passes. To scan the first pass, single element 116 is extended from sensor array 112 while other sensor elements 114 are deactivated and maximally retracted towards the sensor housing, as shown in FIG. 9. Bead guides 132 are extended for engagement with the weld joint, while roller spacers 128 are retracted or adjusted to provide minimum clearance during the scanning of the first pass. Referring now to FIG. 10, for array scanning of the second pass, all sensor array elements are active and held at the same distance from the sensor housing. Roller spacers 128 are extended further from the housing to provide required minimum clearance from second pass B cap surface. Bead guides 132 are retracted.

An exemplary embodiment of eddy current sensor 100 following welding torch 500 at a predetermined standoff distance is shown in FIG. 2. Eddy current sensor 100 generates a signal indicating when a critical discontinuity (e.g., missed seam, lack of side wall fusion, porosity) or defect condition (e.g., alloy composition deviation) is detected. The system processes the discontinuity signal and forwards an eddy current trigger signal to the welding system, which then classifies or otherwise characterizes the trigger signal and corrects the welding process to eliminate the discontinuity or defect condition. The location and size of the eddy current indication is recorded and evaluated as being acceptable or unacceptable. If the indication is unacceptable, it is possible to reposition the welding system with the eddy current sensor 100 in place, repair the indication location, and then reexamine the weld.

Some of the functions of this invention can be demonstrated by computer modeling. The modeled indications in the first and second pass are obtained from planar discontinuities which may be present at one or more of the root (or bottom), the center, or the top of each pass. The pore or volumetric discontinuity is the result of a surface pore barely breaking the top surface. This defect would likely be missed if only visual non-destructive evaluation was conducted. Signals from planar discontinuities with variable height and pores throughout the weld volume were also modeled (not shown) to characterize sensor performance. Modeled signals may be compared to a modeled reference signal from a modeled reference sensor. The reference sensor was physically available and tested in practical trials generating a detectable actual reference signal from representative subsurface discontinuity 0.08" height×0.54" length in a coupon under 0.25" thick plate. The coupon and the plate were made of stainless steel 316L, representative of modeled parent and weld alloy. All discontinuity signals with amplitudes equal or larger than the reference signal are expected to be detected in accordance with use of one of the exemplary eddy current sensor systems as disclosed herein. Of course, it will be appreciated that further adjustment or optimization of one or more of the sensor exciter and receiver components and the controller and analysis components may yield greater or lesser sensitivity to defects in accordance with the various embodiments contemplated herein.

Example: Field Demonstration

The objectives of the field demonstration were to verify how the sensor, equipment and inspection techniques might be integrated with the HLGMAW equipment and existing phased array ultrasonic technique; test the sensor at high temperature; and verify efficacy in a shop setting.

Plates were provided to fabricate at least four welds for the trials. Six plates were used to fabricate three butt welds—Weld 1, Weld 2 and Weld 3. The first pass was initially fabricated. The second pass was later fabricated or deposited on the first pass for each of the welds. The pairs of plates were laser tacked before deposition of the first pass. The plate material was stainless steel 316L. The EC equipment was setup for inspection of the first pass using a single receiver element deployed for inspection of the weld joint (FIG. 9), and second pass using a receiver element array as shown in FIG. 10. During the first pass deposition and data collection, an additional phased array ultrasonic sensor (not shown) was mounted. Only the EC array sensor was monitoring the hot second pass weld deposition. The phased array ultrasonic sensor was not used during the fabrication of the second pass because wet coupling on the surface was unacceptable and a high surface temperature might potentially damage the wedge. The process parameters were varied and inserts (ceramic, copper), and contamination (vacuum grease) were added to the bead in an attempt to produce flaw conditions. Both laser and arc welding processes were used for the first pass, while the second pass was fabricated with only the GMAW process.

Examination of Weld 1 First Pass—Post-Process

The first pass was inspected with eddy current sensor 100 post-process to ensure sensor protruding element 116 would not be exposed to temperatures exceeding 200° C. Measurements indicated that the temperature was in the range from 200 to 300° C. at the sensor location approximately 230 mm behind welding torch.

Evaluation Summary: The weld and no-weld conditions were clearly separated. Visual inspection of cap and root indicated raised cap with possible toe overlap and insufficient root metal drop with possible LOP and/or LOF. Some indications were aligned with laser power interruption, LOP and grease. Numerous indications were identified that might be caused by surface and subsurface features (e.g., Further investigation was deemed required to determine the sources of all indications.

Examination of Weld 2 first initial pass. Post-process.

Eddy current sensor 100 was mounted in the welding equipment following welding torch 500 (FIG. 2), a representative example of which is shown in FIG. 12. Eddy current sensor 100 was ~230 mm behind welding torch 500. An additional copper-tube air cooling line was installed to blow air below eddy current sensor 100 to ensure the device would not overheat especially during inspection of first weld pass B. To further verify weld parameters, an initial short first pass weld was fabricated. Eddy current sensor 100 was not used to monitor the short weld.

Evaluation Summary: The weld and no-weld conditions were clearly separated. Visual inspection of cap and root indicated raised cap with possible toe overlap. Most of root area had acceptable metal drop. Several indications were detected in the short first pass. Indication #3 was very strong. Further investigation was deemed required to determine the sources of all indications.

In an alternate embodiment, this disclosure provides a system and method for nondestructive testing (NDT) of sharp transitional areas using flexible eddy current arrays. Currently known NDT methods encounter problems when testing for surface flaws close to or near sharp transitions in geometry, such as weld toes or edges. This problem is experienced by the most or all industries involved in weld joining and inspection such as heavy manufacturing, energy, infrastructure (e.g., bridges), pipelines, oil and gas, entertainment (e.g., roller-coaster structure) and others. This invention utilizes flexible array eddy current (AEC) probes 200 for structural applications and improves the reliability and performance of the inspection of areas with sharp transitions (e.g., weld toe).

In this context, several methods are currently employed for nondestructive evaluation (NDE) of steel structures and joints with sharp transitions in service and during manufacture. Liquid-penetrant inspection (LPI) requires complete removal of the protective coating and paint. Magnetic particle inspection (MPI) is the method mostly used for steel-welded structures and joints. The MPI techniques will also require removal of the coating. Both methods (MPI and LPI) will produce an excessive number of false indications in the sharp transitional areas due to the challenging geometry of the area. For many surface structures, radiography is not possible to perform due to accessibility requirements. All three techniques provide the length of the flaw only. More often, the flaw depth is the parameter determining structure safe life and repair actions. Ultrasonic (UT) conventional and advanced [phased-array (PA)] techniques are used extensively for length and depth sizing. However, the UT method requires coupling media on the surface (e.g. water, grease). In addition, UT performance for small surface crack detection and sizing may not be adequate, particularly through coatings. Coatings may have to be removed to conduct reliable UT.

The problem addressed by this embodiment of the present invention is experienced across numerous industries including automotive and boat manufacturing, and aviation. The system and method of this invention may be applied to in-service inspection of military and civil structures such as: fatigue cracks in aircraft, repair and refurbishing tanks, and repair and refurbishing ships; automotive gear teeth; non weld applications; oil platforms fatigue crack inspection of welds, attachments and openings; and joining of dissimilar metals such as: drilling risers (steel with Inconel filler X-65), drive shafts (aluminum to steel (very high production rates)), and titanium to Inconel for special forces vehicles.

Figure 13:
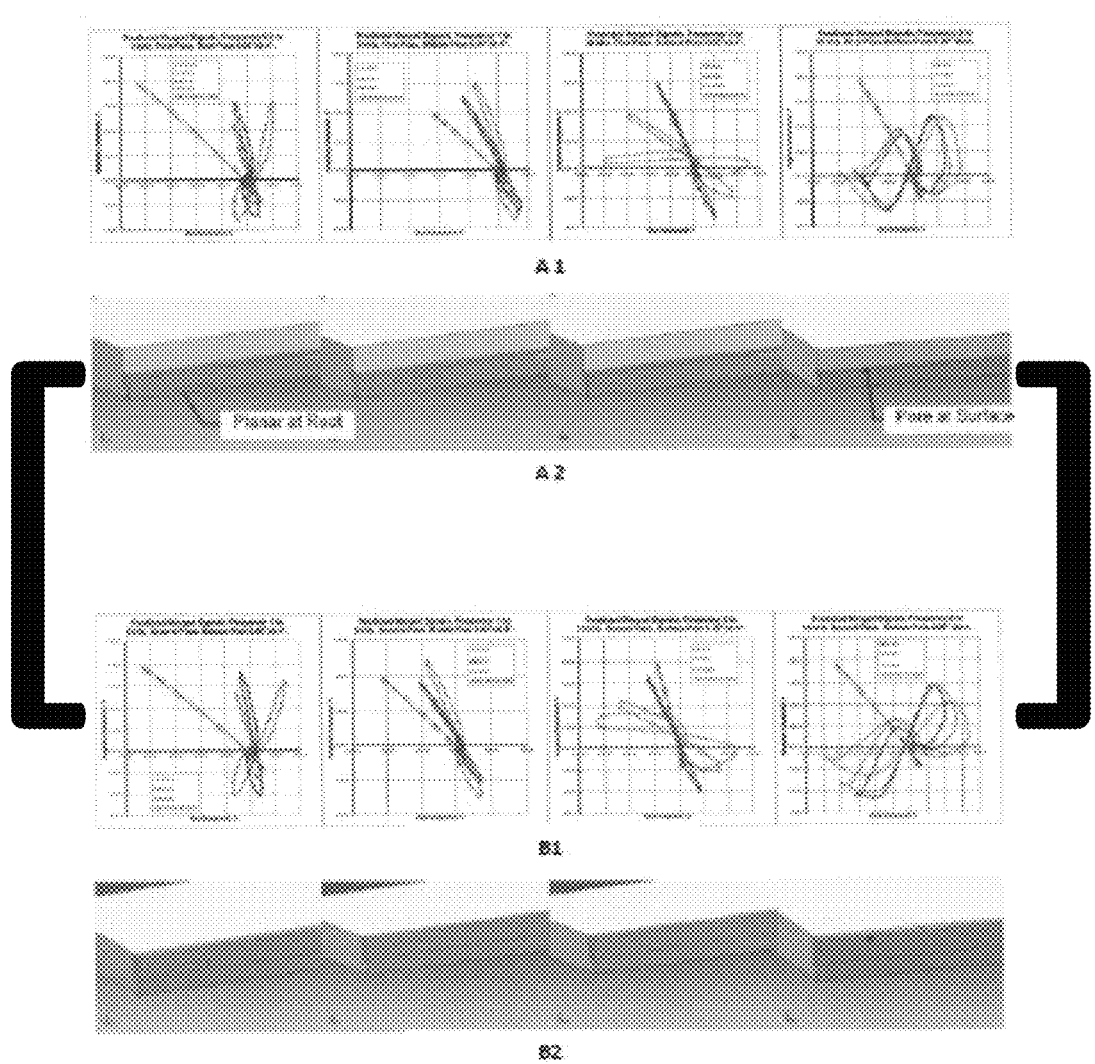
FIG. 13A is a first illustration of an exemplary embodiment of the present invention that includes a probe having a transmitter coil and a receiver coil.
FIG. 13B is a second illustration of the probe of FIG. 13A, wherein a magnetic link has been added to the probe.
FIG. 13C is a third illustration of the probe of FIG. 13A, shown in an alternate orientation relative to the flaw being analyzed.
FIG. 13D is an illustration of an alternate embodiment of the present invention that includes a probe having a transmitter coil and a receiver coil, wherein a magnetic link is mounted on the coils.
FIG. 13E is an illustration of the probe of FIG. 13D, wherein the magnetic link has been removed.
FIG. 13F is an illustration of still another embodiment of the present invention that includes a probe having a transmitter coil and a receiver coil, wherein a magnetic link is mounted on the coils.
FIG. 13G is an illustration of the probe of FIG. 13F, wherein the magnetic link has been removed.
FIG. 13H is an illustration of yet another embodiment of the present invention that includes a probe having a transmitter coil and a receiver coil, wherein a magnetic link is mounted on the coils.
FIG. 13I is an illustration of the probe of FIG. 13H, wherein the magnetic link has been removed.
Figure 13A:
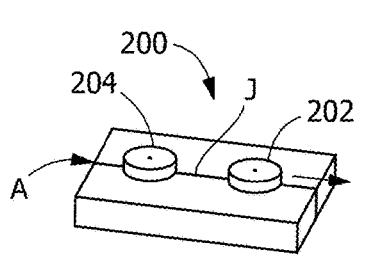
Figure 13B:
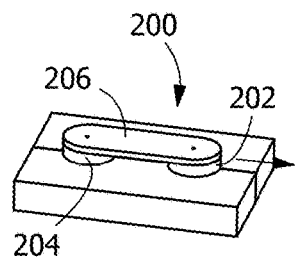
Figure 13C:
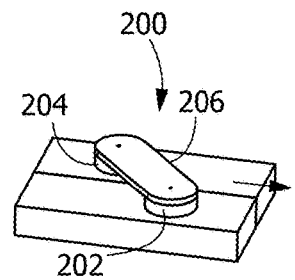
Figure 13D:
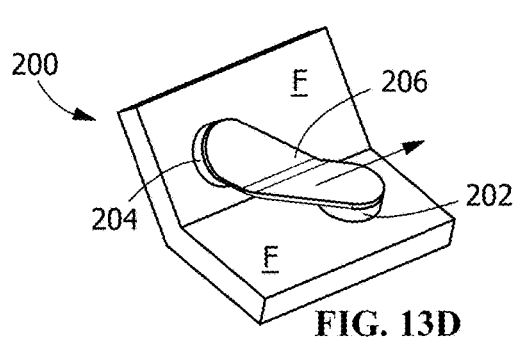
Figure 13E:
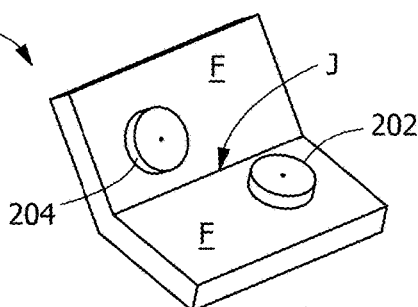
Figure 13F:
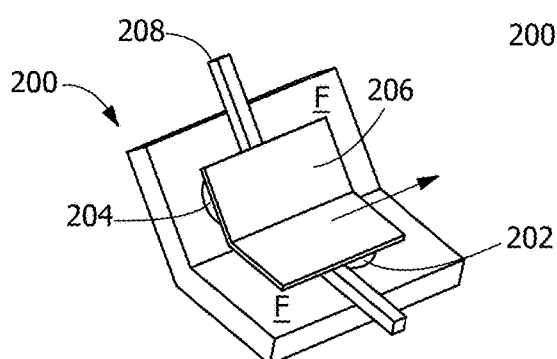
Figure 13G:
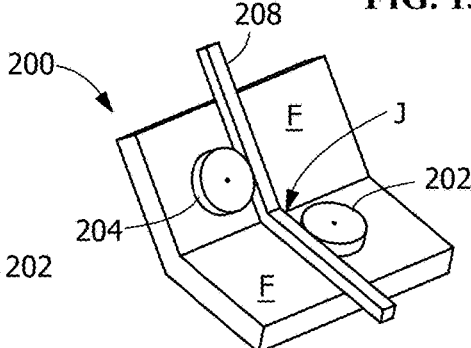
Figure 13H:
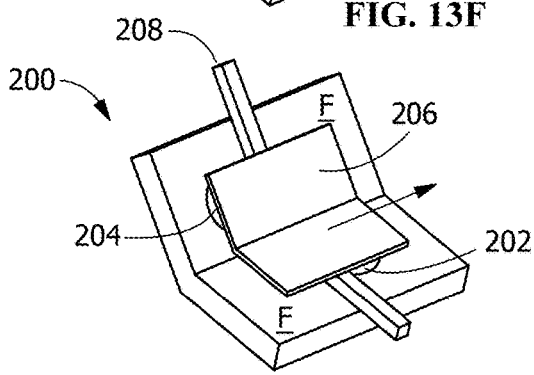
Figure 13I:
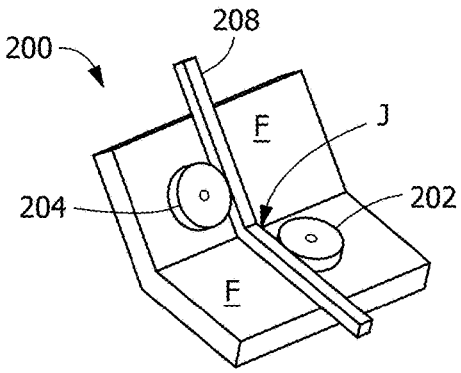
Figure 14B:
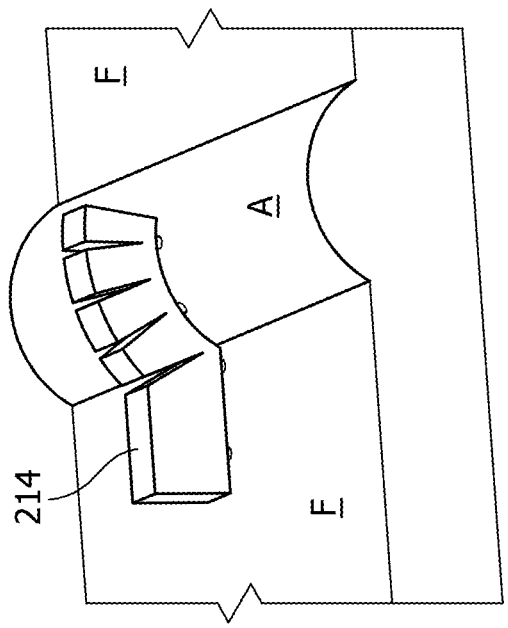
FIG. 14B is an illustration of still another embodiment of the array probe component of the present invention.
Figure 14A:
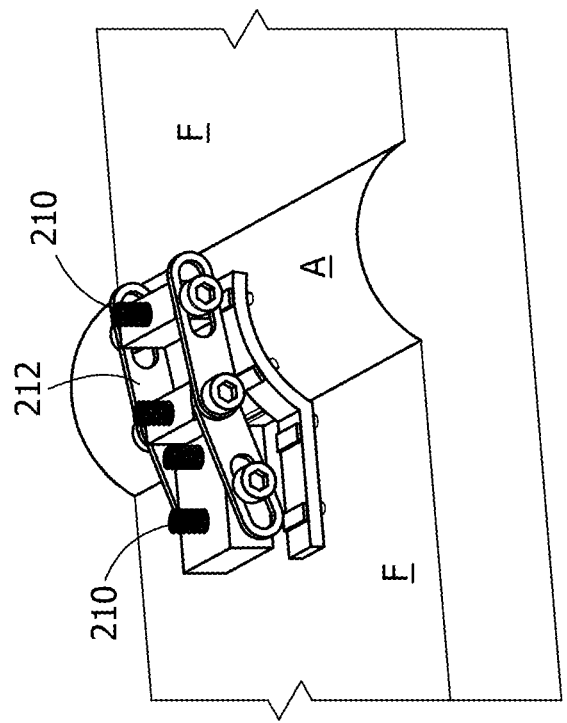
FIG. 14A is an illustration of an alternate embodiment of the array probe component of the present invention.

With reference to FIGS. 13A-I, the current array coil configuration used to detect flaws J parallel to the scan direction on flat surfaces is shown in FIG. 13A. The coils are moved in the direction shown with the thick black arrow. A configuration where one coil is used as transmitter 202 (generating an electromagnetic field) and the other coil as receiver 204 (measuring the changes of the electromagnetic field) is utilized. This configuration calculates a reference signal from a typical flaw 2 mm (length)×1 mm (depth). The probe configuration shown in FIG. 13B illustrates the location of magnetic link 206 used to transfer the magnetic flux from transmitter 202 to receiver 204. During the scanning of welds, the probe coils are located on the parent metal F and weld crown meaning that the probe axis will be skewed with respect to the scan direction. FIG. 13C illustrates this configuration for flat surface and FIGS. 13D-E illustrate a condition where weld crown reinforcement is higher than the parent metal F. FIG. 13E also illustrates the coil position with magnetic link 206 removed. The location of central conductor transmitter 208 is shown in FIGS. 13F-G and FIGS. 13H-I. The coils in FIGS. 13H-I have ferrite cores at the center of the coils. Possible designs of the entire array probe 200 are shown in FIGS. 14A-B, and the scan direction is shown with thick red arrows. The embodiment of FIG. 14A uses springs 210 and fixtures 212 to hold the coils (202 and 204) and magnetic link 206 firmly pressed and conforming to the inspection surface while the embodiment of FIG. 14B uses foam 214 to accomplish the same task.

Several key advantages make this embodiment of the system particularly attractive for this type of structure and joint, including (i) no coating removal is required for inspection purposes; (ii) no couplant or any other media is required to transmit the electromagnetic field from the eddy current coil to the inspected material; (iii) in addition to flaw length data, the eddy current equipment may provide flaw depth data when adequately optimized and calibrated; (iv) array arrangement of eddy current coils makes possible scanning the sharp transitional and surrounding areas in one pass increasing greatly the productivity; (v) the use of magnetic link improves flux transfer from the transmitter coil and central conductor to the receiver when central conductor is applied; (vi) the use of a central conductor improves significantly the sensitivity to small flaws in weld toe area (the eddy current density is increased significantly in the weld toe area as opposed to probes without central conductor); (vii) staggering coils reduces the effect of probe bending; (viii) the location of coils on each side of central conductor allows differential signal to be generated reducing the effect of material structure and surface variations and increasing the probe sensitivity to small flaws; (ix) the use of ferrite cores in the receiver coils increases significantly the sensitivity to longitudinal flaws and redirects the flux to improve the detection of transverse cracks, as well; and (x) the configuration with central conductor and magnetic link is not sensitive to small variations of distance between the central conductor and receiver coils. This invention provides an entirely new way to address the relevant problem, i.e., magnetic link, central conductor, and combination of magnetic link and ferrite cores have not been used for inspection of sharp transitional areas.

Compared to single probes 200 for weld inspection, the array of the present invention is much more productive. If single probe 200 is used, an area of the parent-metal-to-weld-crown transition 12.0"×2.0" will require attachment of probe to a X-Y scanner (scanner must be attached to the metal surface as well) and will take approximately 20 minutes to scan the area with resolution 0.020". An array probe will use only encoder attached to the probe itself (no need for additional scanner) and will scan the same area in one pass in approximately 5 seconds. This is 240 times improvement of productivity. The advantages of array probes are even more pronounced when long weld joints are inspected. The single probe 200 approach will require dividing the weld length to shorter sectors and repositioning of X-Y scanner to each short weld sector for adequate coverage. The array probe with attached encoder is repositioned much faster (simply moved to the next sector/location) because it does require an additional scanner.

While the present invention has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. An eddy current sensor system for approximating real-time monitoring of weld joining processes to detect defects in a weld, the sensor system comprising:
   (a) a housing comprising a base, front and rear faces, and a support frame for retaining and supporting sensor exciter and sensor receiver elements, and comprising at least one alignment element;
   (b) at least one sensor exciter element comprising a coil wound around a ferrite core;
   (c) at least one sensor receiver array, the array comprising at least one sensor element comprising two orthogonally arranged receivers;
   (d) at least one cooling element;
   (e) an elevation system affixed to the housing at its base for supporting the housing on the surface of a welding substrate, and adapted for adjustable elevation of the housing; and
   (f) a controller system engageable with the sensor exciter and receiver elements to control the actuation of the sensor and receipt and transmission of data therefrom for analysis,
   (g) wherein one or more of the housing, the exciter and receiver elements, and the elevation system are rated for temperatures up to at least a preselected temperature.

2. An eddy current sensor system for approximating real-time monitoring of weld joining processes to detect defects in a weld according to claim 1, the sensor system comprising a mechanism permitting at least one element in the array of sensor receiver elements to be extended outward from the other elements in the array to be adjustably positioned in close physical proximity with the surface of a weld joint.

3. An eddy current sensor system for approximating real-time monitoring of weld joining processes to detect defects in a weld according to claim 2, wherein the mechanism permitting at least one element in the array of sensor receiver elements to be extended outward from the other elements in the array to be adjustably positioned in close physical proximity with the surface of a weld joint comprises a spring.

4. An eddy current sensor system for approximating real-time monitoring of weld joining processes to detect defects in a weld according to claim 1, wherein the exciter has a U-shaped ferrite core.

5. An eddy current sensor system for approximating real-time monitoring of weld joining processes to detect defects in a weld according to claim 1 one or more coils wound with a good electrical-conductor wire, a coil having a ferrite core, a giant magnetic resistive sensor, and a Hall effect sensor.

6. An eddy current sensor system for approximating real-time monitoring of weld joining processes to detect defects in a weld according to claim 1, wherein the cooling element comprises within the housing one or a combination of vents, interior passages for flow of cooling fluid, and input valves for receiving fluid air flow from external cooling lines.

7. An eddy current sensor system for approximating real-time monitoring of weld joining processes to detect defects in a weld according to claim 1, wherein at least the housing is formed of material having sufficient heat resistance, good electrical conductivity, and other desirable properties suitable for use in a welding shop selected from the group including magnetic carbon steel and non-magnetic alloys such as copper and brass.

8. An eddy current sensor system for approximating real-time monitoring of weld joining processes to detect defects in a weld according to claim 1, wherein the orthogonally arranged first and second receiver elements are oriented for positioning relative to a weld joint such that the first receiver element registers changes in an electromagnetic field normal to the weld joint, and the second receiver element registers changes in the electromagnetic field parallel to the weld joint.

9. A method for examining weld joints during or immediately following a weld process applied to the joint for detecting surface and subsurface flaws in one or more of a first, second, and any subsequent weld pass, where only the top or cap surface of each pass would be accessible for testing, the method comprising:
  (a) mounting an eddy current sensor system in-line with at least one weld component selected from a laser-beam welding component, a gas-metal-arc welding, and a hybrid laser gas metal arc welding component, welding component and positioned at a distance that ranges from immediately proximate to the welding component to a distance from the welding component sufficient to limit restrict exposure of the eddy current sensor from local thermal conditions exceeding a preselected temperature, the eddy current sensor system comprising;
    (i) a housing comprising a base, front and rear faces, and a support frame for retaining and supporting sensor exciter and sensor receiver elements, and comprising at least one alignment element;
    (ii) at least one sensor exciter element comprising a coil wound around a ferrite core;
    (iii) at least one sensor receiver comprising at least two orthogonally arranged receiver elements, each element comprising a receiver;
    (iv) at least one cooling element;
    (v) an elevation system affixed to the housing at its base for supporting the housing on the surface of a welding substrate, and adapted for adjustable elevation of the housing;
    (vi) a controller system engageable with the sensor exciter and receiver elements to control the actuation of the sensor and receipt and transmission of data therefrom for analysis;
  (b) activating the sensor and the welding component and operating the system in at least one of a first and a second mode,
    (i) wherein the first mode of operation comprises deploying from the eddy current sensor a single receiving element consisting of two orthogonal X and Z receiver coils to inspect at least one weld pass of a weld joint having narrow beads/grooves, wherein the element is adapted for positioning in close proximity to the weld joint, the position ranging from direct contact with the weld joint up to 10 mm above the weld joint; and
    (ii) wherein the second mode of operation comprises deploying an array of two or more receiver elements consisting of two orthogonal X and Z receiver coils to inspect at least one weld pass of a weld joint having relatively wide open beads, wherein each of the two or more elements is adapted for positioning in close proximity to the weld joint, the position ranging from direct contact with the weld joint up to 10 mm above the weld joint; and
  (c) analyzing data from each of the at least first and second operational modes to identify any weld defects.

10. The method for examining weld joints according to claim 9, wherein the eddy current sensor system comprises a mechanism permitting at least one element in the array of sensor receiver elements to be extended outward from the other elements in the array to be adjustably positioned in close physical proximity with the surface of a weld joint.

11. The method for examining weld joints according to claim 10, wherein the mechanism permitting at least one element in the array of sensor receiver elements to be extended outward from the other elements in the array to be adjustably positioned in close physical proximity with the surface of a weld joint comprises a spring.

12. The method for examining weld joints according to claim 9, wherein the cooling element of the eddy current sensor system comprises within the housing one or a combination of vents, interior passages for flow of cooling fluid, and input valves for receiving fluid air flow from external cooling lines.

13. The method for examining weld joints according to claim 9, wherein the housing of the eddy current sensor system is formed of aluminum, magnetic carbon steel, and non-magnetic alloys.

14. The method for examining weld joints according to claim 9, wherein the orthogonally arranged first and second receiver elements of the eddy current C sensor system are oriented for positioning relative to a weld joint such that the first receiver element registers changes in an electromagnetic field normal to the weld joint, and the second receiver element registers changes in the electromagnetic field parallel to the weld joint.

* * * * *